(12) United States Patent
Varga et al.

(10) Patent No.: US 11,707,541 B2
(45) Date of Patent: Jul. 25, 2023

(54) PIPETTE CAROUSEL WITH GERMICIDAL LAMP

(71) Applicant: MTC Bio, Inc., Sayreville, NJ (US)

(72) Inventors: Edward Varga, Union, NJ (US); Walter Demsia, Holmdel, NJ (US)

(73) Assignee: MTC BIO, INC., Sayreville, NJ (US)

( * ) Notice: Subject to any disclaimer, the term of this patent is extended or adjusted under 35 U.S.C. 154(b) by 176 days.

(21) Appl. No.: 17/374,761

(22) Filed: Jul. 13, 2021

(65) Prior Publication Data

US 2021/0338855 A1 Nov. 4, 2021

Related U.S. Application Data

(62) Division of application No. 16/375,991, filed on Apr. 5, 2019, now Pat. No. 11,141,497.

(51) Int. Cl.
*A61L 2/10* (2006.01)
*A61L 2/00* (2006.01)
*B01L 9/00* (2006.01)
*A61L 2/26* (2006.01)

(52) U.S. Cl.
CPC .............. *A61L 2/0047* (2013.01); *A61L 2/10* (2013.01); *A61L 2/26* (2013.01); *B01L 9/54* (2013.01); *A61L 2202/11* (2013.01); *A61L 2202/23* (2013.01)

(58) Field of Classification Search
CPC . A61L 2/0047; A61L 2/10; A61L 2/26; A61L 2202/11; A61L 2202/23; B01L 9/54
See application file for complete search history.

(56) References Cited

U.S. PATENT DOCUMENTS

| | | | | |
|---|---|---|---|---|
| 4,625,119 A | * | 11/1986 | Murdock, III | A61L 2/10 250/455.11 |
| 4,806,770 A | * | 2/1989 | Hylton | A47K 1/09 250/455.11 |
| 7,213,603 B2 | * | 5/2007 | Pinsky | A61L 2/10 250/455.11 |
| 2018/0029040 A1 | * | 2/2018 | Driscoll | B01L 9/54 |

* cited by examiner

*Primary Examiner* — Timothy C Cleveland
(74) *Attorney, Agent, or Firm* — FisherBroyles, LLP; Susan M. Oiler (57) ABSTRACT

An apparatus for decontaminating and storing lab instruments such as pipettes. A carousel feature of the apparatus provides convenient access and allows multiple items to be decontaminated at the same time. The ultraviolet lamp directs UV radiation to surface contaminations of the instruments and effectively eliminates various microorganisms.

20 Claims, 8 Drawing Sheets

PIPETTE CAROUSEL WITH GERMICIDAL LAMP

RELATED APPLICATIONS

This application is a divisional application of U.S. application Ser. No. 16/375,991, filed Apr. 5, 2019.

FIELD

The present disclosure relates to an apparatus for decontaminating and storing lab instruments such as pipettes.

BACKGROUND

Device sterilization processes, and in particular lab instrument decontamination processes, often involve dis-assembling, washing and drying to remove the contaminants. For instance, in labs focusing on cell culture, microbiology, molecular studies or PCR, even if extra care is exercised to prevent contamination, pipettes used by multiple technicians can easily become carriers of stray DNA, mycoplasma or other micro-organism contamination. It is therefore necessary to dis-assemble the pipette, subject them to cleaning solutions, and remove residual moisture or solvents in the pipette components. Sometimes recalibration of the pipette may be required.

Accordingly, apparatuses and methods for storing devices/instruments and decontaminating microorganisms would be desirable.

SUMMARY

It would be desirable to provide an apparatus and method that address at least some of the issues discussed above, as well as other potential issues. Moreover, it would be beneficial to furnish an integrated system for storage and decontamination, wherein no separate device is required.

Accordingly, apparatuses and methods are disclosed for storage and decontamination purposes substantially as shown in and/or described in connection with at least one of the figures, and as set forth more completely in the claims.

More specifically, examples of the present disclosure are generally directed to apparatuses, and methods for decontaminating and storing a device or instrument, wherein no separate germicidal device is required and wherein an ultraviolet lamp member and auxiliary components are integrated into a storage apparatus.

The apparatus disclosed herein provides effective and efficient decontamination for various devices or instruments. Biological contaminations including for example DNA, mycoplasma, bacteria, fungi and viruses can be reduced, in exemplary implementations, by up to 99%. There is no need to dis-assemble or recalibrate after cleaning and no waiting for devices or instruments to cool before using.

The apparatus of the present disclosure generally includes a base, a housing connected to the base and having a bottom and a sidewall, a rotatable cap having a plurality of openings and forming an enclosure with the housing, an ultraviolet light source in the enclosure, and a reflector positioned along interior surface of the side wall for reflecting light from the light source.

Each of the openings on the cap provides access to the enclosure, where an object to be decontaminated is irradiated under UV light. The openings can be configured in different ways to suit the positioning and entry of objects of different shapes. For instance, a pipette having a handle portion and a shaft portion will need to have the handle portion secured to the opening while the shaft portion is exposed to UV light inside the housing for decontamination. Therefore, the opening is sized accordingly to pass the shaft. Meanwhile, the wider handle portion is held at the opening without being inserted deep into the housing so that the pipette can be readily retrieved. This can be achieved via means such as a properly sized guiding channel in the opening or a securing means such as an expandable clip.

Two, three, four, five, six or more openings can be positioned in the cap. As explained above, the shape and size of the openings may be the same or different depending on the intended use. In some implementations, the openings are aligned in a circular fashion on the cap. This alignment coupled with a rotation means for the cap provides a carousel feature for the apparatus and allows a technician or a purchaser to easily select the correct object simply by rotating the cap. To facilitate the rotation, the cap can include a handle for initiating the rotating and stopping the rotation. In an exemplary implementation, the handle is a protrusion or a stick at the center of the cap.

The cap is mounted on top of the housing to form an enclosure. In some implementations, the cap rotates together with the housing attached thereto, while the base remains stationary. The base may include for example a retainer, a circular guide or a channel in the center, which holds the bottom of the housing in position and facilitate the rotation of the housing. In some implementations, only the cap rotates and the housing remains stationary. The top edge of the side wall of the housing may include a retainer, circular guide or channel to guide the rotation of the cap.

The cap may also include a handle for controlling the rotation. The handle is preferably positioned at the center of the cap.

The UV light source can be placed at any suitable position in the enclosure. Preferably, the light source is at the center of the base. In some implementations, the light source irradiates light having wavelength ranging from about 240 to about 280 nm. In some implementations, the light has a wavelength of about 254 nm. In some implementations, the light source is a UV-C lamp. The wattage of the lamp ranges for example from about 200 to about 600 watts.

The reflector is circularly aligned along the interior of the side wall. In an exemplary implementation, the reflector provides a 360° reflection of the UV light. The exact height and angle of the reflector relative to the base can be adjusted if necessary depending on the location of the object to be decontaminated. In some implementations, the reflector contains a polymer surface coating on a metal substrate. In an exemplary implementation, the surface coating is polyester and the metal substrate for the surface coating is aluminum.

To prevent the UV light from escaping the enclosure, additional structural features and special materials can be incorporated to the apparatus. In some implementations, the cap has a protrusion towards the light source. The protrusion serves to block UV light escaping through the openings. In an exemplary implementation, the protrusion has a tubular shape. Regardless of the actual shape of the protrusion, it can be transparent, translucent, or opaque. Other polymers can also be used for the construction of the protrusion as long as it helps to filter off UV light. In some implementations, the protrusion is a tube made of a material comprising or consisting essentially of polycarbonate.

The side wall of the housing can be similarly made from a UV resistant or UV stabilized material. In some implementations, the side wall is made of a material comprising or consisting essentially of polycarbonate. In some implementations, the side wall is transparent or semi-transparent so that the position of the portion of the object (e.g. shaft of the pipette) is visible to a user. In an exemplary implementation, the housing has a "frosted" or translucent but not very transparent surface. In some implementations, the height of the reflector is about ⅓, ½ or ⅔ of the height of the side wall.

The apparatus also includes a control circuit for controlling the operation of the unit. The length of time, the wavelength of the UV light, and/or the intensity of the light can be controlled with the circuit.

In some implementations, the object to be decontaminated is a pipette having a handle portion connected to a shaft portion, and wherein the opening is configured to pass the shaft portion into the enclosure and hold the handle portion.

In some implementations, the opening comprises expandable clip for holding the object. In some implementations, the openings are aligned in the cap in a circular fashion.

In some implementations, the cap further comprises a handle for controlling rotation of the cap. In some implementations, the handle protrudes along a vertical central axis of the housing.

In some implementations, the cap further comprises a protrusion towards the base, wherein the width and the length of the protrusion is sized to reduce escaping of the light through the openings.

In some implementations, the protrusion and the housing are independently made from a polymer such as polycarbonate.

In some implementations, the protrusion is of tubular shape and comprises or consists essentially of polycarbonate.

In some implementations, the side wall of the housing is circular and the housing rotates together with the cap.

In some implementations, the reflector is in the shape of a circular wall and comprises a polyester surface coating.

In some implementations, the light source is positioned along the vertical axis. In some implementations, the light source is attached to the base. In some implementations, the light source irradiates light having wavelength ranging from about 240 to about 280 nm. In some implementations, the light source irradiates light having wavelength of about 254 nm.

In some implementations, the apparatus further comprises a control circuit for controlling operation of the light source.

Another aspect of the present disclosure provides a method of eliminating or reducing contaminating microorganisms or biological contaminants from at least a portion of an object. The method includes exposing the portion to be decontaminated to the UV light in the enclosure of the apparatus of the present disclosure. The length of time in exposing to UV light depends on the specific instrument and the contaminants thereon. In some implementations, the time ranges from about 1 to about 60 minutes, from about 5 to about 35 minutes, or from about 10 to about 30 minutes. The wavelength of the light is similarly adjustable depending on the contaminants to be removed. In some implementations, the method utilizes light having wavelength ranging from about 240 to about 280 nm. In some implementations, the wavelength is fixed at about 254 nm.

Various types of biological contaminants can be reduced or eliminated. Non-limiting examples of the biological contaminants include DNA, mycoplasma, bacteria, fungi, and viruses.

In some implementations, the biological contaminant contains DNA, which can be destroyed by the UV light. In some implementations, the biological contaminant includes bacteria and the UV light damages and destroys DNA of the bacteria.

In some implementations, the object is a pipette having a handle portion connecting to a shaft portion, and the shaft portion is exposed to the light. In some implementations, the biological contaminant is bacteria, and DNA of the bacteria is damaged or destroyed by the UV light.

BRIEF DESCRIPTION OF THE DRAWINGS

The drawings referenced herein form a part of the specification. Features shown in the drawings are meant as illustrative of some, but not all, embodiments of the present disclosure, unless otherwise explicitly indicated, and implications to the contrary are otherwise not to be made. Although in the drawings like reference numerals correspond to similar, though not necessarily identical, components and/or features, for the sake of brevity, reference numerals or features having a previously described function may not necessarily be described in connection with other drawings in which such components and/or features appear.

DETAILED DESCRIPTION OF THE INVENTION

Some examples of the present disclosure will now be described more fully hereinafter with reference to the accompanying drawings, in which some, but not all examples of the disclosure are shown. Indeed, various aspects of the disclosure may be embodied in many different forms and should not be construed as limited to the examples set forth herein. Rather, these examples are provided so that this disclosure will be thorough and complete and will fully convey the scope of the disclosure to those skilled in the art. Like reference numerals refer to like elements throughout.

As used herein, "and/or" means any one or more of the items in the list joined by "and/or". As an example, "x and/or y" means any element of the three-element set, e.g., {(x), (y), (x, y)}.

The following detailed description is merely illustrative in nature and is not intended to limit the implementations of the subject matter or the application and uses of such implementations. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Referring more particularly to the drawings, examples of the present disclosure include apparatus and methods for storage and/or decontamination purposes. The apparatus is adaptable to various types of objects including for example medical devices and research instruments. Without sacrificing its storage utility, the apparatus is structurally and functionally advantageous over conventional devices by offering effective decontamination. In particular, the decontamination process does not require a separate germicidal device and removes biological contaminants, including for example, DNA, mycoplasma, bacteria, fungi and viruses.

While the apparatus disclosed herein is often described in the context of lab equipment, such as pipettes of various kinds, its application is extendible to other objects carrying microorganism.

Figure 1:
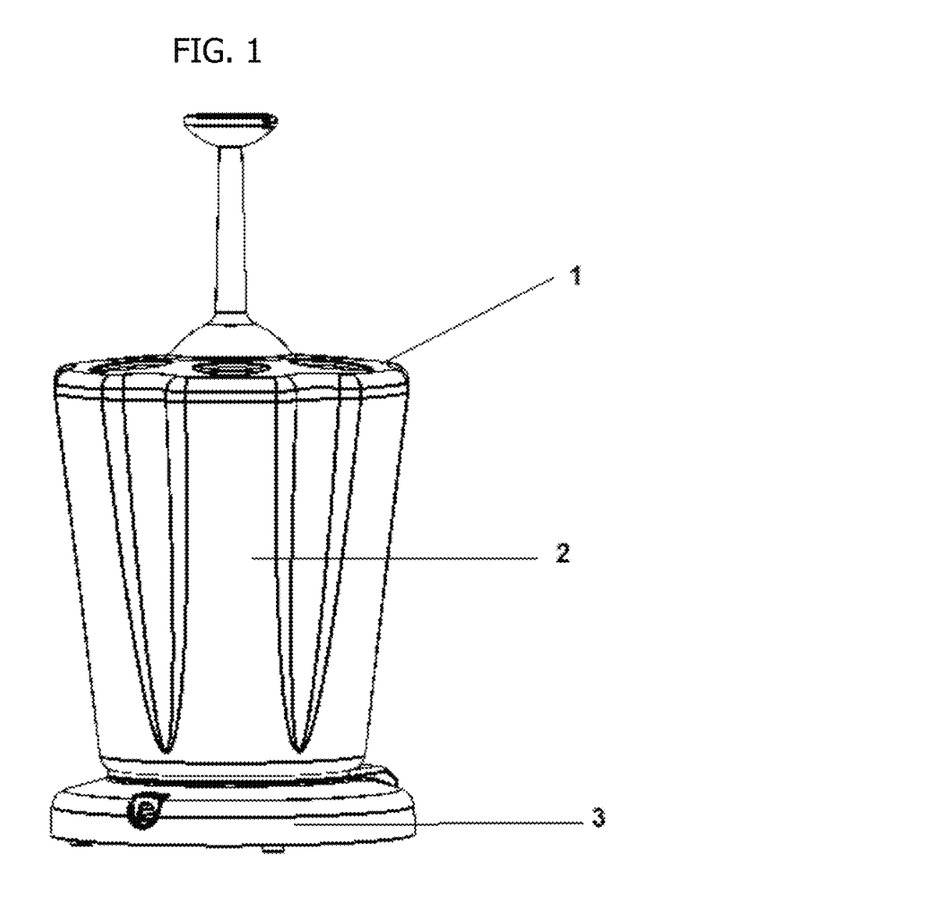
FIG. 1 illustrates an exemplary implementation of a decontamination apparatus in accordance with the present disclosure having a cap, a housing and a base.

Turning to FIG. 1, an exemplary implementation of a decontamination apparatus includes cap 1, housing 2 and base 3. The apparatus serves decontamination and storage function for pipette 4.

Figure 2:
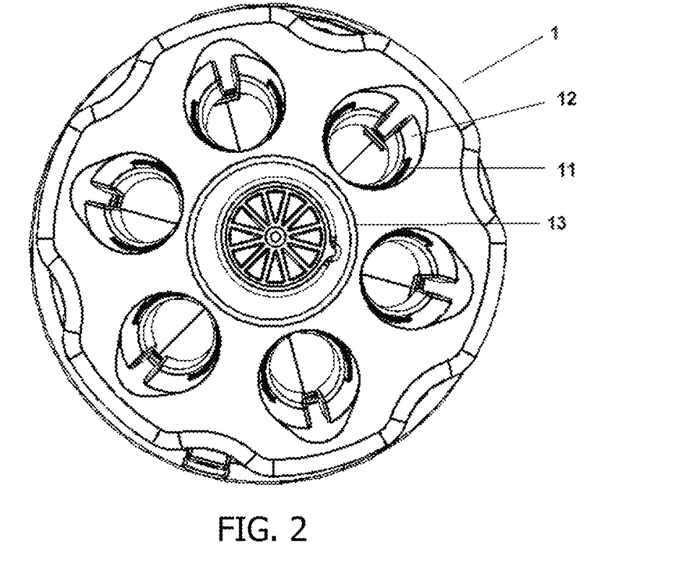
FIG. 2 illustrates a top view of an exemplary implementation of a decontamination apparatus in accordance with the present disclosure, having a cap with multiple opening, clips, and a handle.
Figure 3:
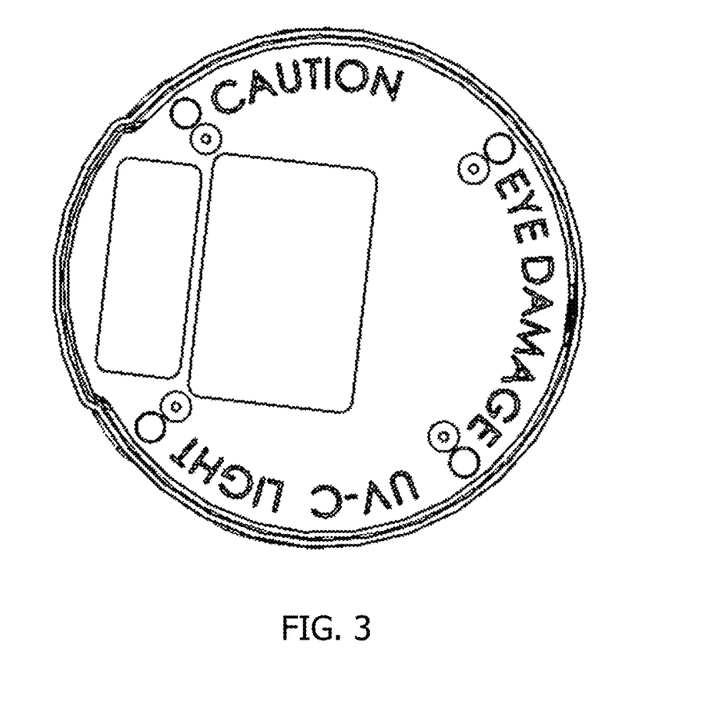
FIG. 3 illustrates a bottom view of an exemplary implementation of a decontamination apparatus in accordance with the present disclosure.

Referring to FIG. 2, an exemplary apparatus of the top view includes cap 1, opening 11, clip 12, and handle 13. The shape and size of the opening can certainly be adjusted depending on the object (e.g. pipette) to be decontaminated. While the figure illustrates 6 openings, the cap can be configured to have fewer or more opening. If necessary, the openings can be staggered on the cap and positioned in different distances to the center of the cap. Clip 12 is shown to be under opening 11. The actual positioning and shape of the clip may vary. Clip 12 can also be replaced with a ring or guide tube sized to pass only the shaft of the pipette. While handle 13 is in the center of the cap, one or more handles can be placed near the perimeter of the cap. The handle can have a knob or grip for ease of control and moving the apparatus. FIG. 3 shows a bottom view of the apparatus.

Figure 4:
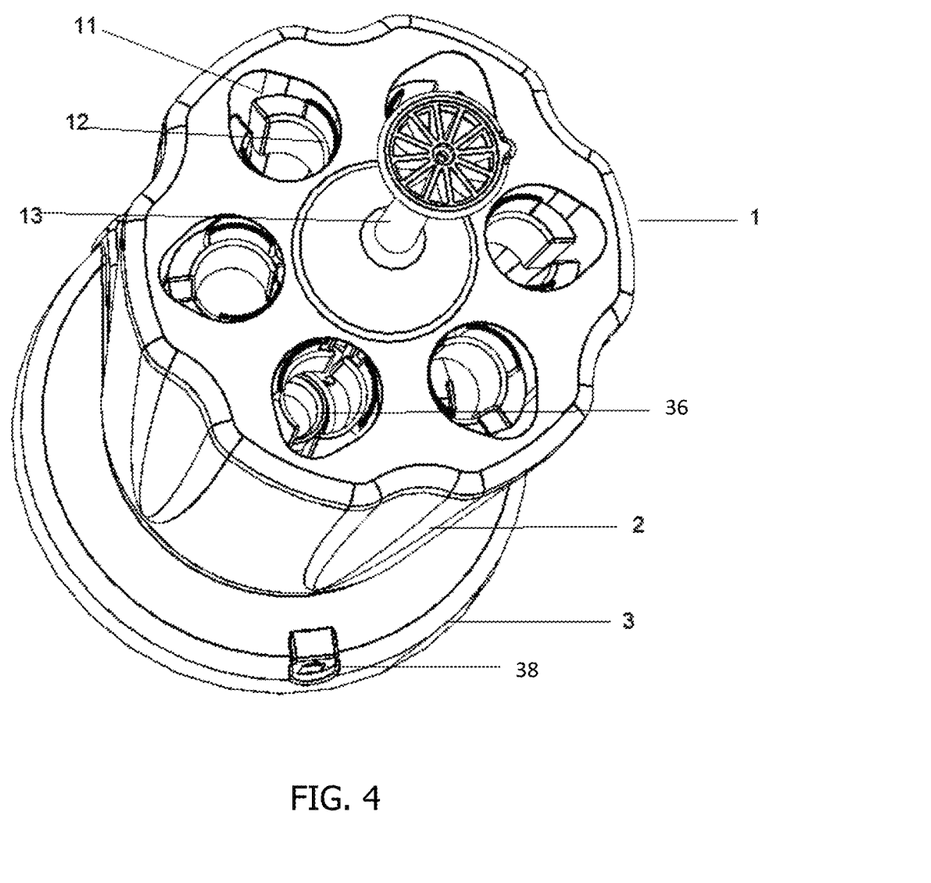
FIG. 4 illustrates a top view of an exemplary implementation of a decontamination apparatus in accordance with the present disclosure, having a cap with multiple opening, clips, a handle, and a protrusion, and a base including a socket for UV lamp.

Referring to FIG. 4, an exemplary implementation of cap 1 includes opening 11, clip 12, handle 13, and protrusion 14. Base 3 includes power inlet 38 and socket 36 for installing UV lamp.

Figure 5:
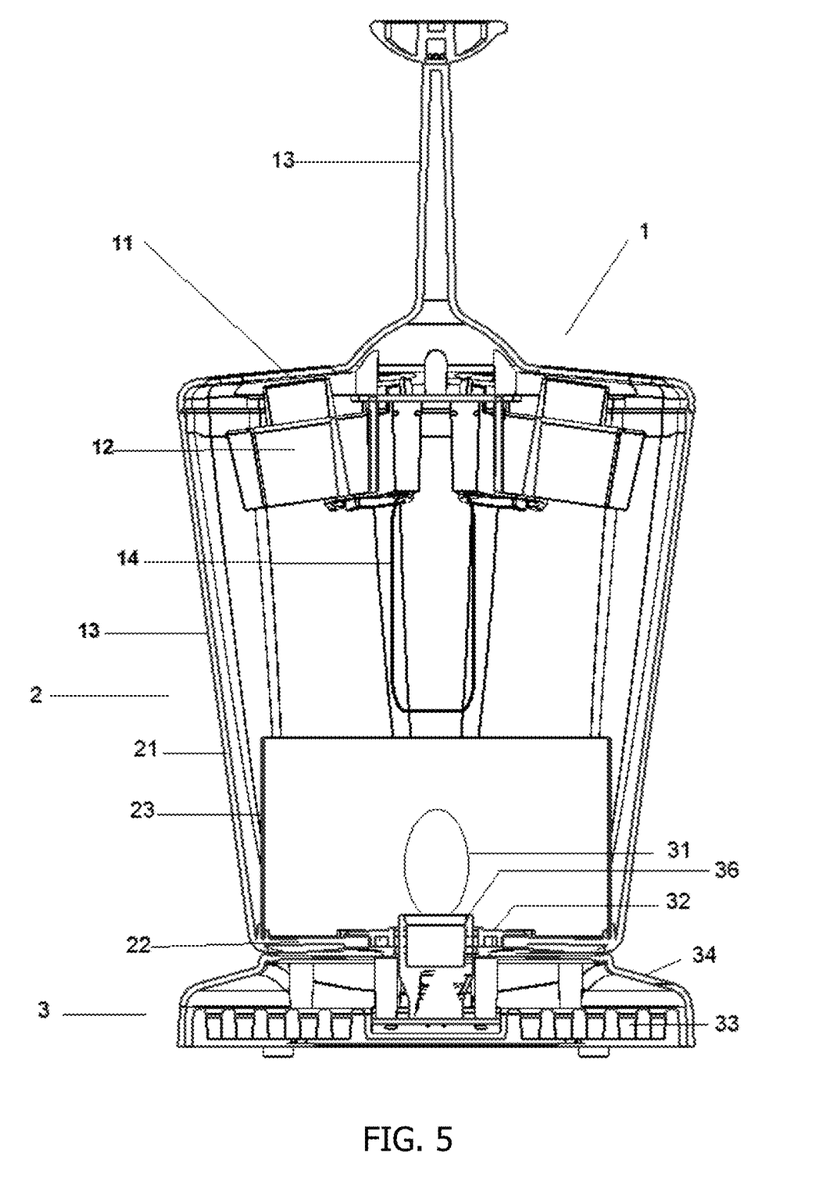
FIG. 5 illustrates a sectional view of an exemplary implementation of a decontamination apparatus in accordance with the present disclosure components having a cap, housing, and base, wherein the cap includes multiple opening, clips, a handle, and a protrusion; the housing includes a side wall, a bottom and a reflector; and the base includes a light source, a retainer and a weight.

Referring to FIG. 5, an exemplary apparatus includes cap 1, housing 2 and base 3. Cap 1 further includes opening 11, clip 12, and handle 13. Housing 2 includes side wall 21, bottom 22 and reflector 23. Base 3 includes lamp 31, retainer 32, weight 33, base cover 34, and socket 36. The handle portion 41 of pipette 4 is secured at opening 11. Meanwhile, shaft portion 42 passes through opening 11 into the enclosure and is exposed to UV light.

Figure 6:
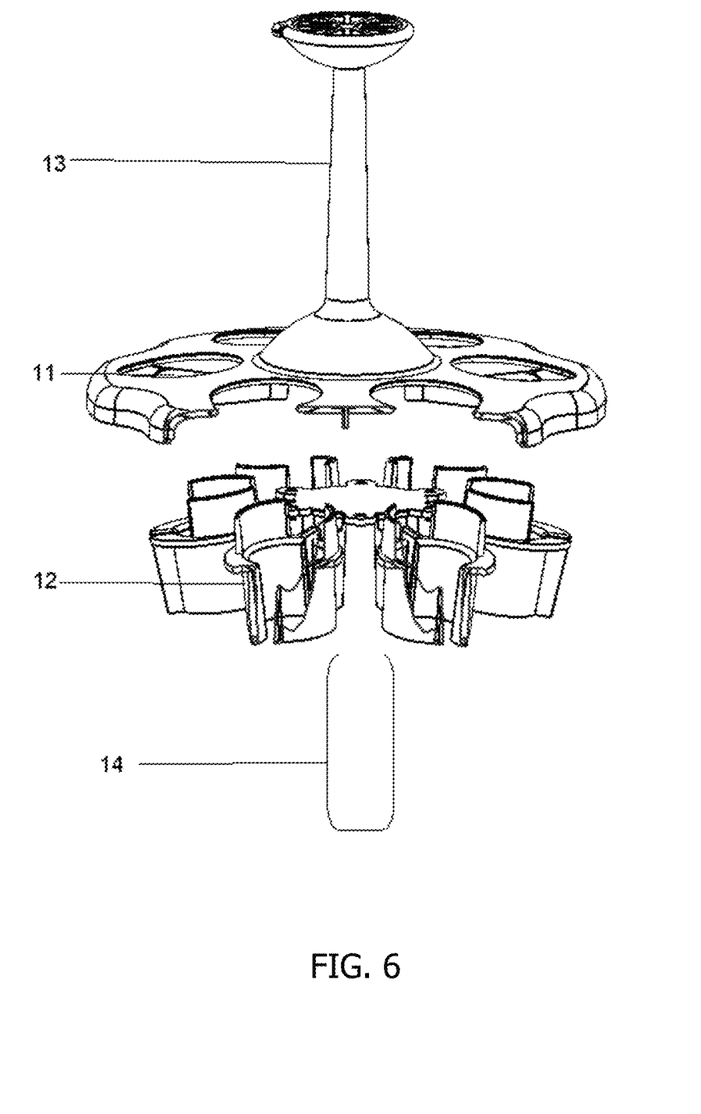
FIG. 6 illustrates a partial exploded view of an exemplary implementation of a cap and components of a decontamination apparatus in accordance with the present disclosure.

Referring to FIG. 6, an exemplary structure of cap 1 includes opening 11, clip 12 attached to opening 11, handle 13 and protrusion 14. The cap can be sealed to the housing at the edge and form an enclosure, which rotates around a central axis of the housing. In some implementations, the top edge of the housing side wall in contact with the perimeter of the cap forms a retainer and guide the rotation of the cap while the housing remains stationary. The tube shaped protrusion 14 is positioned along the vertical central axis of the housing and serves to block or reduce escaping light through opening 11. As long it serves such a purpose, any protrusion from the cap can be incorporated into the cap. For instance, a protrusion may include a rod with a round shield at the end. Of course, the protrusion should not interfere with the entry of the component/portion into the enclosure and subsequent UV decontamination. In some implementations, at least the area of the protrusion for blocking UV light is made from a material comprising or consisting essentially of polycarbonate.

Figure 7:
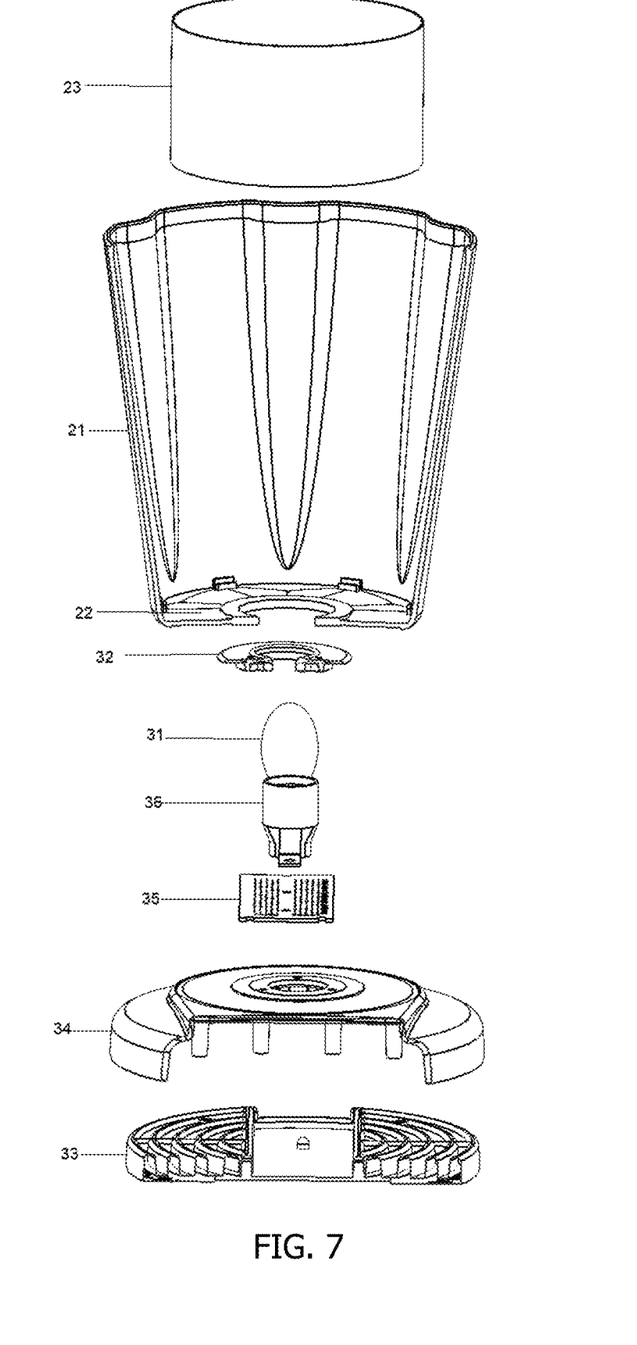
FIG. 7 illustrates a partial exploded view of an exemplary implementation of a base and housing of a decontamination apparatus in accordance with the present disclosure.

Referring to FIG. 7, an exemplary implementation includes components for the base and the housing. Specifically, housing components include side wall 21, bottom 22 and reflector 23. Sidewall 21 is preferably made from a material that block or reduce "leaking" of UV light. In some implementation, side wall 21 comprises polycarbonate. The height and angle of reflector 23 is such that maximum amount of light is reflected to the area of the object that needs to be decontaminated. The reflector is preferably aligned as a circular wall and thus provides reflection from the entire 360° angle. In some implementations, the reflector mirror comprises a metal (e.g., aluminum) substrate or backing and a polymer (e.g., polyester) surface coating.

Figure 8:
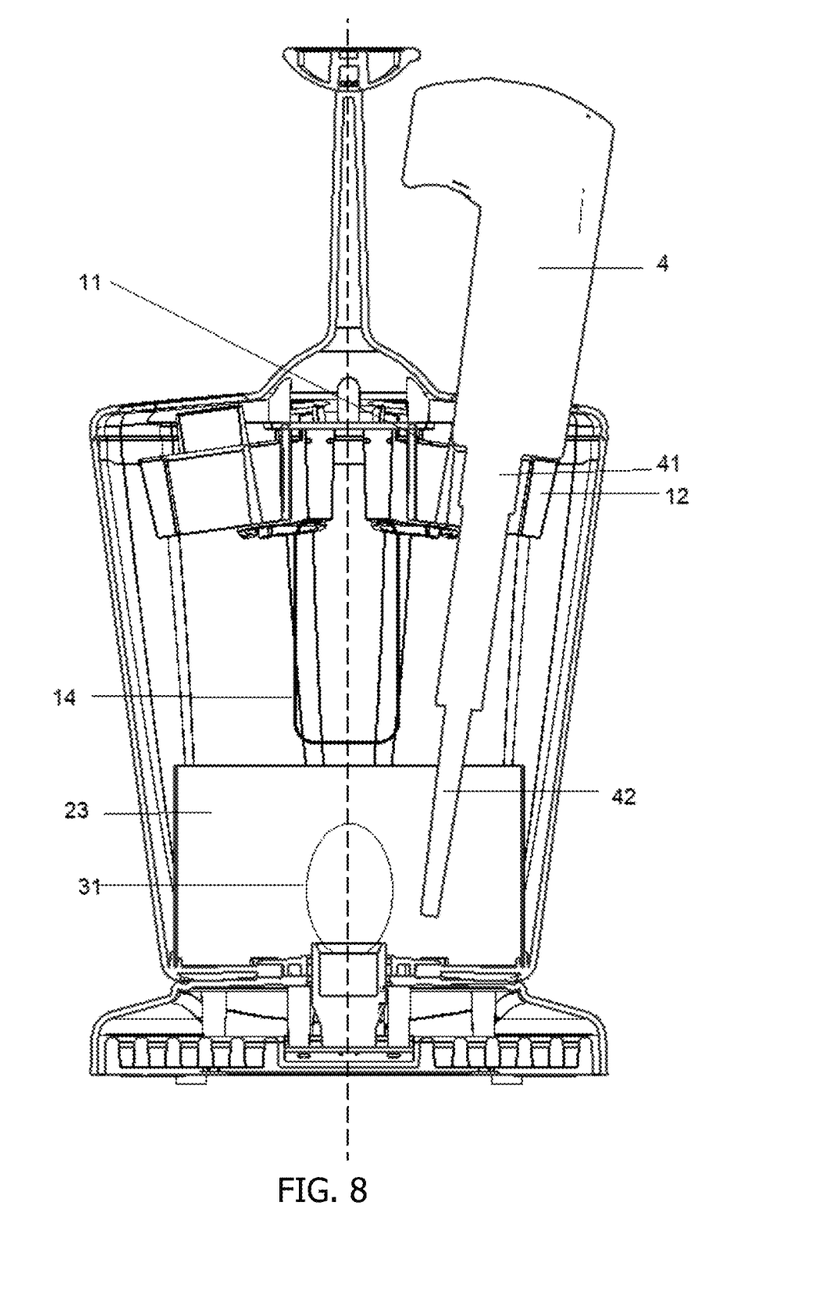
FIG. 8 illustrates a sectional view of a pipette in an exemplary implementation of a decontamination apparatus in accordance with the present disclosure.

Referring to FIG. 8, an exemplary implementation shows pipette being position in the apparatus. The wider handle portion 41 is being held in opening 11 by clip 12. The narrower shaft portion goes into the enclosure and is exposed to UV light from lamp 31. Reflector 23 assists with a 360° radiation. Protrusion 14 reduces light escaping through opening 11.

The housing is held in place to the base via retainer 32, which also guides the rotation of the housing. Besides retainer 32, the base includes lamp 31, weight 33, base cover 34, control circuit 35, and socket 36. Power inlet and control button/knob (manual or digital) can also be included in the base. In combination with the control circuit, the control button sets the time and/or power of UV irradiation. Weight 33 helps stabilize the unit. In some implementations, the apparatus is battery powered or contains backup battery which adds portability to the device.

EXAMPLE

Figure 9:
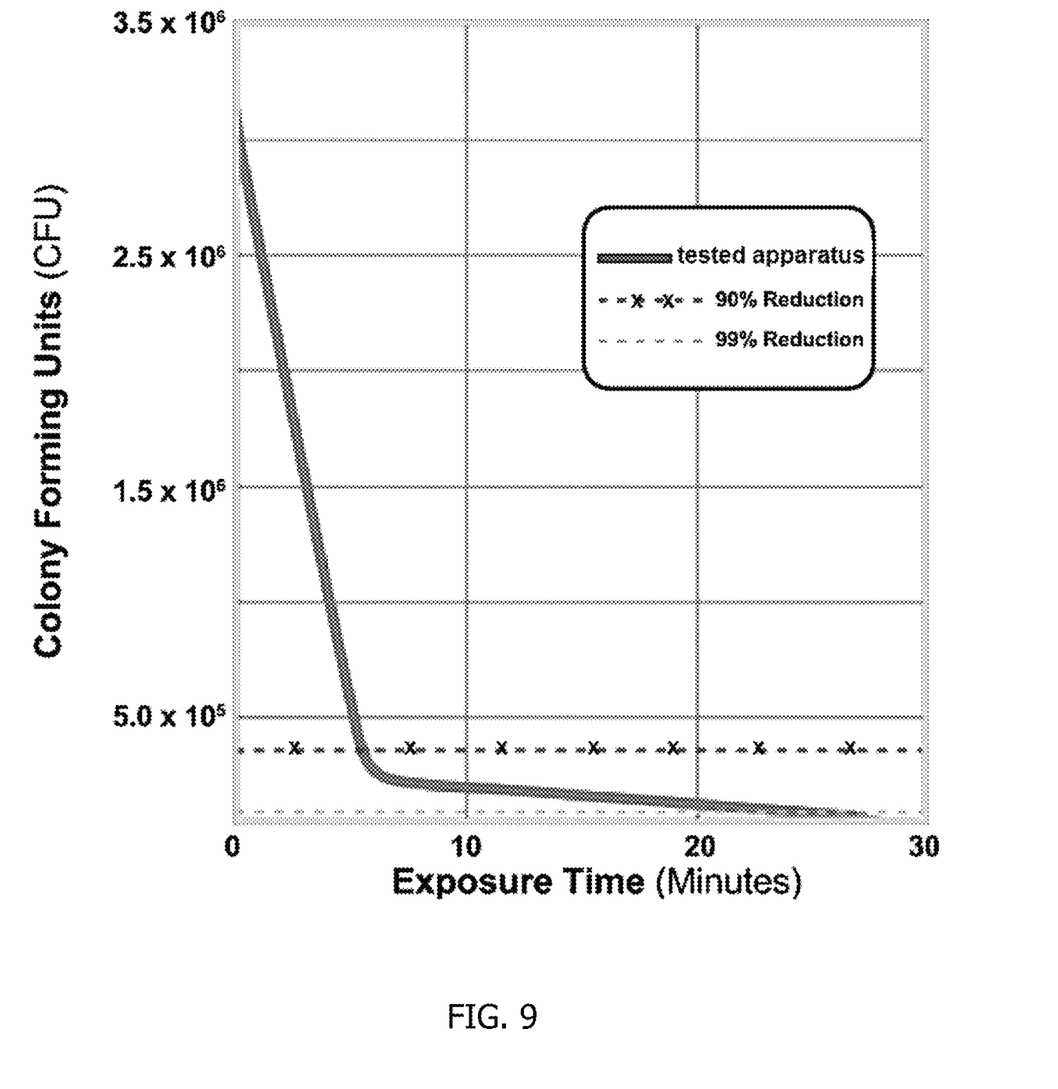
FIG. 9 is a graphical representation of the germicidal effect of the apparatus on *S. aureus*.

In one non-limiting example of an exemplary implementation of a decontamination apparatus in accordance with the present disclosure, an irradiating 254 nm UV light was tested in for its microorganism-killing effect. Adjustable pipettes were inoculated with *S. aureus* and placed in the decontamination apparatus. The UV radiation was directed around the pipette shaft. With the assistance of the reflector, the decontamination apparatus provided 360° coverage, exposing the entire shaft to the germicidal lamp's effect. The preset timer activated the light for 28 minutes. The pipettes were removed from the apparatus at different time during the decontamination cycle and after the cycle and then rinsed to remove any residual contamination. The rinses were then plated and the CFU counted to determine the effectiveness of the germicidal lamp. As shown in FIG. 9, it was determined that the length of time was effective for reducing *S. aureus* by up to 99%.

Many modifications and other examples of the disclosure set forth herein will come to mind to those skilled in the art to which this disclosure pertains, having the benefit of the teachings presented in the foregoing descriptions and the associated drawings. Therefore, it is to be understood that the disclosure is not to be limited to the specific examples disclosed and that modifications and other embodiments are intended to be included within the scope of the appended claims.

Moreover, although the foregoing descriptions and the associated drawings describe aspects of the disclosure in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus for decontaminating pipettes, comprising:
    a base;
    a housing connected to the base; wherein the housing defines an internal chamber and comprises:
        a first closed end defining a plurality of openings each shaped to receive therethrough a working end of a pipette and to hold a handle portion of the pipette,
        an array of expandable clips positioned within the internal chamber proximate the first closed end with one each in alignment with one each of the plurality of openings, and
        an elongate, tubular protrusion positioned centrally within the array of expandable clips and extending toward the base; and
    an ultraviolet light source received in the internal chamber of the housing; and
    wherein the elongate, tubular protrusion terminates more proximate the ultraviolet light source than the array of expandable clips and has an area that blocks ultraviolet light, thereby preventing ultraviolet light from escaping from the internal chamber through the plurality of openings.

2. The apparatus of claim 1, wherein the array of expandable clips is an annular array disposed about a vertical central axis of the housing.

3. The apparatus of claim 2, wherein each clip of the array of expandable clips is C-shaped.

4. The apparatus of claim 2, wherein each expandable clip is oriented at an angle relative to the vertical central axis with a most radial outward portion being closer to the base than a most radial inward portion.

5. The apparatus of claim 2, wherein each of the plurality of openings is generally pear-shaped with the wider bottom portion oriented toward the vertical central axis.

6. The apparatus of claim 1, wherein an area of the elongate, tubular protrusion blocks UV light and said area comprises polycarbonate material.

7. The apparatus of claim 1, wherein each of the plurality of openings comprises a guiding channel extending into the internal chamber.

8. The apparatus of claim 1, wherein the housing comprises a cap defining the plurality of openings, wherein the cap is removable.

9. The apparatus of claim 8, wherein the housing is rotatable relative to the base about an axis of rotation, and the cap has a handle for controlling rotation of the housing.

10. The apparatus of claim 9, wherein the handle is aligned with the axis of rotation.

11. The apparatus of claim 1, wherein the elongate, tubular protrusion and the housing are each made of polycarbonate.

12. The apparatus of claim 1, wherein the elongate, tubular protrusion has a closed end proximate the ultraviolet light source.

13. The apparatus of claim 1, comprising a reflector proximate an interior surface of the housing in a surrounding relationship to the ultraviolet light source.

14. The apparatus of claim 13, wherein the reflector provides 360° reflection of the ultraviolet light and comprises a polyester surface coating.

15. The apparatus of claim 1, wherein the housing is rotatable relative to the base about an axis of rotation.

16. The apparatus of claim 15, wherein the ultraviolet light source is aligned with the axis of rotation.

17. The apparatus of claim 15, wherein the bottom of the housing defines an aperture, and a retainer is seated in the aperture; wherein the retainer guides rotation of the housing relative to the base.

18. The apparatus of claim 1, wherein the base comprises an electrical light socket having the ultraviolet light source received therein and a control circuit for controlling said electric light socket.

19. The apparatus of claim 1, wherein the ultraviolet light source irradiates light having wavelength ranging from about 240 to about 280 nm.

20. The apparatus of claim 1, wherein the ultraviolet light source irradiates light having wavelength of about 254 nm.

* * * * *